United States Patent
Loh et al.

(10) Patent No.: US 9,180,442 B2
(45) Date of Patent: Nov. 10, 2015

(54) POROUS GRAPHENE OXIDE MATERIALS

(71) Applicant: National University of Singapore, Singapore (SG)

(72) Inventors: Kian Ping Loh, Singapore (SG); Chen Liang Su, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 14/407,409

(22) PCT Filed: Jun. 18, 2013

(86) PCT No.: PCT/SG2013/000249
§ 371 (c)(1),
(2) Date: Dec. 11, 2014

(87) PCT Pub. No.: WO2013/191654
PCT Pub. Date: Dec. 27, 2013

(65) Prior Publication Data
US 2015/0119581 A1   Apr. 30, 2015

Related U.S. Application Data

(60) Provisional application No. 61/660,870, filed on Jun. 18, 2012.

(51) Int. Cl.
| | |
|---|---|
| *B01J 35/00* | (2006.01) |
| *B01J 21/18* | (2006.01) |
| *B01J 37/06* | (2006.01) |
| *B01J 37/12* | (2006.01) |
| *B01J 23/22* | (2006.01) |
| *B01J 23/40* | (2006.01) |
| *B01J 23/44* | (2006.01) |
| *B01J 23/52* | (2006.01) |
| *B01J 23/70* | (2006.01) |
| *B01J 27/20* | (2006.01) |
| *B01J 35/10* | (2006.01) |
| *C01B 31/04* | (2006.01) |
| *C07C 211/04* | (2006.01) |
| *C07C 211/28* | (2006.01) |
| *C07D 409/12* | (2006.01) |
| *B82Y 40/00* | (2011.01) |
| *B01J 37/34* | (2006.01) |

(52) U.S. Cl.
CPC .............. *B01J 35/0033* (2013.01); *B01J 21/18* (2013.01); *B01J 23/22* (2013.01); *B01J 23/40* (2013.01); *B01J 23/44* (2013.01); *B01J 23/52* (2013.01); *B01J 23/70* (2013.01); *B01J 27/20* (2013.01); *B01J 35/10* (2013.01); *B01J 37/06* (2013.01); *B01J 37/12* (2013.01); *C01B 31/043* (2013.01); *C07C 211/04* (2013.01); *C07C 211/28* (2013.01); *C07D 409/12* (2013.01); *B01J 35/002* (2013.01); *B01J 35/1014* (2013.01); *B01J 35/1019* (2013.01); *B01J 35/1023* (2013.01); *B01J 35/1028* (2013.01); *B01J 35/1038* (2013.01); *B01J 35/1042* (2013.01); *B01J 35/1047* (2013.01); *B01J 35/1057* (2013.01); *B01J 35/1061* (2013.01); *B01J 35/1066* (2013.01); *B01J 37/343* (2013.01); *B82Y 40/00* (2013.01); *C01B 2204/32* (2013.01); *C01P 2006/14* (2013.01)

(58) Field of Classification Search
CPC .................................................... B01J 35/0033
USPC ............................................................ 549/59
See application file for complete search history.

(56) References Cited

FOREIGN PATENT DOCUMENTS

CN         101912777 A      12/2010

OTHER PUBLICATIONS

Zhou "Hydrothermal Dehydration for the 'Green' Reduction of Exfoliated Graphene Oxide to Graphene and Demonstration of Tunable Optical Limiting Properties" Chemistry of Materials vol. 21, pp. 2950-2956. 2009.
Rourke, et al., "The real graphene oxide revealed: Stripping the oxidative from the graphene-like sheets", Angew. Chem., Int. Ed., 50, 3173-3177 (2011).
Fan, et al., "Deoxygenation of Exfoliated Graphite Oxide under Alkaline Conditions: A Green Route to Graphene Preparation", Advanced Materials, 2008, vol. 20, pp. 4490-4493.
Gengler, et al., "A Roadmap to High Quality Chemically Prepared Graphene", Journal of Physics D: Applied Physics, 2010, vol. 43, 374015.
Pei, et al., "The Reduction of Graphene Oxide", Carbon, 2012, vol. 50, pp. 3210-3228.
Stankovich, et al., "Synthesis of Graphene-based Nanosheets via Chemical Reduction of Exfoliated Graphite Oxide", Carbon, 2007, vol. 45, pp. 1558-1565.
Zhan, et al., "Electronic Structure of Graphite Oxide and Thermally Reduced Graphite Oxide", Carbon, 2011, vol. 49, pp. 1362-1366.
Zhou, "The Reduction of Graphene Oxide", Carbon, 2012, vol. 50, pp. 3210-3228.
Rourke, et al., "The real graphene oxide revealed: Stripping the oxidative debris from the graphene-like sheets", Angew. Chem., Int. Ed., 50, 3173-3177 (2011).

*Primary Examiner* — Taofiq A Solola
(74) *Attorney, Agent, or Firm* — Cesari and McKenna, LLP

(57) ABSTRACT

A method of preparing a porous graphene oxide material. The method includes the steps of: (1) preparing graphene oxide sheets from graphite at 40 to 170° C.; (2) providing a graphene oxide suspension containing the graphene oxide sheets; (3) heating the graphene oxide suspension with a base at 25 to 300° C. for 0.1 to 48 hours to obtain base-treated graphene oxide sheets; and (4) heating a mixture of the base-treated graphene oxide sheets and an acid at 25 to 300° C. for 0.1 to 48 hours to yield the porous graphene oxide material. Also disclosed are novel porous graphene oxide materials and methods of using these materials as catalysts.

22 Claims, 4 Drawing Sheets

(a)

(b)

(a) FTIR of graphene oxide sheets (b) FTIR of ba-GO3

POROUS GRAPHENE OXIDE MATERIALS

CROSS REFERENCE TO RELATED APPLICATIONS

This application is the National Stage of International Application No. PCT/SG2013/000249, filed on Jun. 18, 2013, which claims the benefit of U.S. Provisional Application No. 61/660,870, filed on Jun. 18, 2012. The contents of both applications are hereby incorporated by reference in their entirety.

BACKGROUND

Graphene oxide sheets, inexpensively prepared from graphite, have been used in various reactions as catalysts in place of expensive metal catalysts.

However, they typically have very low catalytic reactivity and require a catalyst loading of 200-400 wt % to substantially covert a reactant to a desired product. See Dreyer et al., Angewandte Chemie, 122, 6965-68 (2010). This low reactivity limits widespread use of graphene oxide catalysts.

SUMMARY

This invention is based on an unexpected discovery of a method for preparing certain porous graphene oxide materials that are highly catalytic and highly magnetic.

One aspect of this invention relates to a method of preparing a porous graphene oxide material including the steps of: (1) preparing graphene oxide sheets from graphite at 40-170° C.; (2) providing a graphene oxide suspension containing the graphene oxide sheets; (3) heating the graphene oxide suspension with a base at 25 to 300° C. for 0.1 to 48 hours to obtain base-treated graphene oxide sheets; and (4) heating a mixture of the base-treated graphene oxide sheets and an acid at 25 to 300° C. for 0.1 to 48 hours to yield the porous graphene oxide material. The weight ratio of the base to the graphene oxide sheets is 1:1 to 50:1, the weight ratio of the acid to the graphene oxide sheets is 1:1 to 50:1, the base in the graphene oxide suspension has a concentration of 0.01 to 50 N, and the acid in the mixture has a concentration of 0.01 to 50 N.

Another aspect of this invention relates to a porous graphene oxide material prepared by the method described above. The porous graphene oxide material can contain a second catalyst.

A further aspect of this invention relates to a porous graphene oxide material that have a pore size of 0.2 to 100 nm, a pore volume of 0.01 to 5 mL/g, a surface area of 20 to 2600 $m^2/g$, a C/O molar ratio of 2/1 to 10/1, and a —$COO^-$ content of 0.

Still within the scope of this invention is a process of carrying out a chemical reaction by agitating a reaction medium containing (1) a reactant or reactants and (2) a catalyst that is the porous graphene oxide material described above. Examples of the chemical reaction include an oxidation reaction, a reduction reaction, a Suzuki coupling reaction, an oxygen reduction reaction, and an oxidation-reduction tandem reaction.

The details of one or more embodiments of the invention are set forth in the description and the drawings below. Other features, objects, and advantages of the invention will be apparent from the description, the drawings, and the claims.

DETAILED DESCRIPTION

Figure 1:
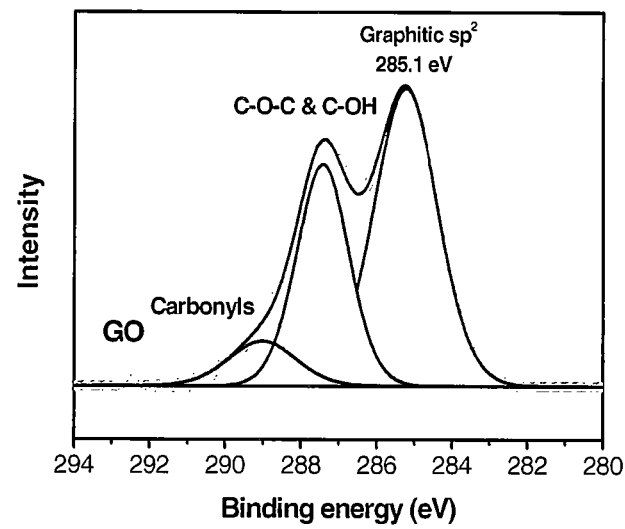
FIG. 1 shows X-ray photoelectron spectra of the graphene oxide sheets and a graphene oxide material, i.e., ba-GO3, both of which were prepared following the procedures described in Example 3 below.
Figure 1:
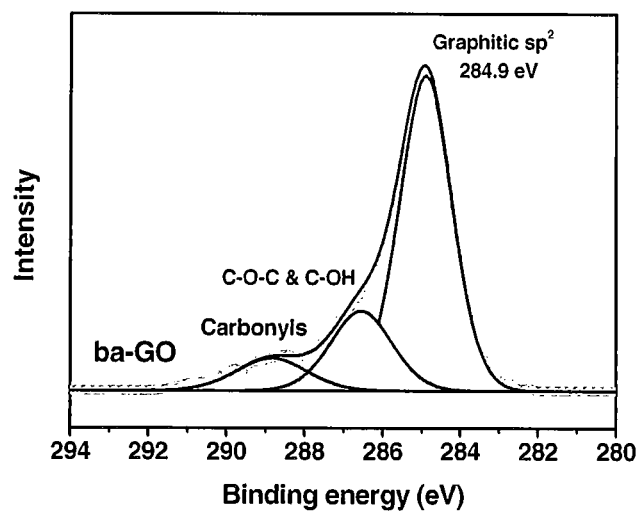

Disclosed herein is a method of preparing a porous graphene oxide material, which is useful as a catalyst for chemical reactions, e.g., oxidation reactions.

According to this method, the porous graphene oxide material is prepared by heating graphene oxide sheets with a base and then with an acid.

Graphene oxide sheets can be prepared from graphite using methods well known in the art. See Hummers et al., Journal of American Chemical Society, 80, 1339 (1958); and Jia et al., Tetrahedron, 67, 4431-34 (2011). Typically, to obtain graphene oxide sheets, graphite flakes are treated with sodium nitrate, concentrated sulfuric acid, and $KMnO_4$ at 40-170° C. (e.g., 50 to 160° C. and 60 to 120° C.) for 0.1 to 48 hours (e.g., 0.5 to 24 hours and 0.5 to 5 hours), and subsequently washed with a hydrogen peroxide solution. The resultant graphene oxide sheets are collected and washed for the next step, i.e., base treatment. Not to be bounded by any theory, high temperature helps generate in the graphene oxide sheets small pores, which are subsequently enlarged by the base and acid treatments described below.

The graphene oxide sheets thus obtained are suspended in a solvent to obtain a graphene oxide suspension. Suitable solvents include, but are not limited to, water, dimethylformamide, dimethyl sulfoxide, N-methyl-e-pyrrolidone, methanol, ethanol, acetonitrile, and a combination thereof. The concentration of the graphene oxide sheets in the suspension can be 0.01 to 20 g/L (e.g., 0.05 to 8 g/L and 0.1 to 4 g/L).

The graphene oxide suspension is heated with a base at 25 to 300° C. (e.g., 60 to 170° C. and 100 to 120° C.) for 0.1 to 48 hours (e.g., 1 to 24 hours and 2 to 10 hours) to obtain base-treated graphene oxide sheets. Examples of suitable bases include NaOH, KOH, LiOH, $Na_2CO_3$, $CsCO_3$, $K_3PO_4$, $NaHCO_3$, n-BuLi, t-BuOK, amines (e.g., triethylamine, isopropylamine, and N,N-diisopropylethylamine), pyridine, bipyridines, and a combination thereof. The concentration of the base in the suspension is 0.01 to 50 N (e.g., 0.02 to 20 N and 0.05 to 10 N). The weight ratio of the base to the graphene oxide sheets is 1:1 to 50:1 (e.g., 2:1 to 25:1 and 3:1 to 10:1).

The base-treated graphene oxide sheets are optionally separated (e.g., by centrifugation and by filtration) and washed with water.

The base-treated graphene oxide sheets are then mixed with an acid and heated at 25 to 300° C. (e.g., 60 to 170° C. and 100 to 120° C.) for 0.1 to 48 hours (e.g., 1 to 24 hours and 2 to 10 hours) to obtain a porous graphene oxide material. Examples of suitable acids include HCl, HBr, HI, $H_2SO_4$ and its salts (e.g., $LiHSO_4$ and $(NH_4)_2SO_4$), $HNO_3$, carboxylic acids (e.g., tartaric acid and trifluoroacetic acid), sulfonic acids (e.g., methanesulfonic acid and toluenesulfonic acid), phosphoric acid and its salts (e.g., $KH_2PO_4$), $P_2O_5$, metal chlorides (e.g., $AlCl_3$, $TiCl_4$, $ZrCl_4$, and $FeCl_3$), and a combination thereof. The concentration of the acid in the mixture is 0.01 to 50 N (e.g., 0.02 to 20 N, 0.05 to 10 N, 0.01 to 0.8 N, and 0.02 to 0.6 N). The weight ratio of the base to the graphene oxide sheets is 1:1 to 50:1 (e.g., 2:1 to 25:1 and 3:1 to 10:1).

Both the base and acid treatments may be carried out in a microwave-assistant process or in a hydrothermal process.

As pointed out above, both the base and acid treatments enlarge pores that are initially generated during the preparation of graphene oxide sheets from graphite. The base treatment also removes contaminants and chemically reduces epoxide and hydroxyl groups. On the other hand, the acid treatment acidifies the base-treated graphene oxide sheets. Typically, carboxylate anions (i.e., —COO$^-$) are neutralized to carboxylic acid groups (i.e., —COOH) and phenolate anions (i.e., ArO$^-$, Ar being an aromatic radical) are neutralized to phenol groups (i.e., ArOH) in the acid treatment. As a result, the porous graphene oxide material is free of both carboxylate anions and phenolate anions. The base and acid treatments, in combination, unexpectedly yield a porous graphene oxide material that is highly catalytic in many chemical reactions including oxidations, reductions, Suzuki coupling reactions, oxygen reduction reactions, and oxidation-reduction tandem reactions.

Note that the porous graphene oxide material prepared by the method described above is highly magnetic.

Also disclosed herein is a porous graphene oxide material prepared by the method described above or by any other method. The porous graphene oxide material has a pore size of 0.2 to 100 nm (e.g., 0.5 to 50 nm and 1 to 20 nm), a pore volume of 0.01 to 5 mL/g (e.g., 0.05 to 1 mL/g and 0.1 to 0.4 mL/g), a surface area of 20 to 2600 m$^2$/g (e.g., 50 to 1000 m$^2$/g and 100 to 600 m$^2$/g), a C/O molar ratio of 2/1 to 10/1 (e.g., 5/2 to 8/1 and 3/1 to 6/1), and a —COO$^-$ content of 0.

The porous graphene oxide material, a catalyst, can be free of another catalyst or a metal. On the other hand, it can contain a second catalyst to serve as a bifunctional catalyst. More specifically, metal nanoparticles can be added to the porous graphene oxide material to form a bifunctional catalyst for tandem oxygen activation and hydrogen activation. Examples of suitable second catalysts include Pd, Pt, Au, Cu, V$_2$O$_5$, Co, Rh, Ru, Ni, and Fe.

Further disclosed herein is a process of carrying out a chemical reaction by agitating a reaction medium containing a reactant or reactants, and a catalyst that is the porous graphene oxide material described above. Examples of the chemical reaction include an oxidation reaction, a reduction reaction, a Suzuki coupling reaction, an oxygen reduction reaction, and an oxidation-reduction tandem reaction.

Take the oxidation reaction for example. It is carried out by agitating a reaction medium containing a catalyst that is a porous graphene oxide material described above, a reactant, and an oxidizing agent at 25 to 160° C. to obtain a product. The oxidizing agent can be oxygen, hydrogen peroxide, meta-chloroperoxybenzoic acid, or tert-butyl hydroperoxide. Using the porous graphene oxide material, which is 1 to 200 wt % (e.g., 1 to 40% and 2 to 20%) of the reactant, one can convert 20 to 98% (e.g., 50-98%) of the reactant to the product.

The oxidation reaction can be carried out in open air (i.e., using oxygen as the oxidizing agent) and free of any solvent.

The term "oxidation reaction" refers to oxidation of alcohols, amines, alkenes, and alkanes, oxidative coupling of amines, and cross-dehydrogenative-coupling reactions. For examples of oxidation reactions, see Su et al., Angewandte Chemie International Edition, 50, 657-60 (2011); Liu et al., ChemComm, 47, 10148-50 (2011); Chu et al., Organic & Biomolecular Chemistry, 8, 4716-19 (2010); and Dreyer et al., Chemical Science, 2, 1233-40 (2011).

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are incorporated by reference in their entirety.

Example 1

A porous graphene oxide material, i.e., ba-GO1, was prepared following the procedure described below.

Fabrication of Graphene Oxide Sheets

Graphene oxide sheets, as a starting material to prepare the porous graphene oxide material, were prepared from graphite flakes. First, graphite flakes (3 g) were added to a flask and stirred in an ice bath. Sodium nitrate (3 g) and concentrated sulfuric acid (135 mL) were added, followed by addition of KMnO$_4$ (18 g) over 2 hours. Once the resultant mixture was homogeneous, it was heated in an oil bath at 35° C. and stirred for 1 hour to form a thick paste, to which water (240 mL) was added. This mixture was stirred for 1 hour at 90° C., cooled to ambient temperature, and then diluted with water (600 mL), followed by slow addition of a 30 wt % hydrogen peroxide solution (18 mL). The resultant suspension was filtered and then washed with a 3 wt % HCl solution (1000 mL). The filtrate was centrifuged at 13,000 rpm for 30 minutes, resulting in separation of a clear supernatant liquid and a thick yellow liquid. The clear supernatant liquid was decanted. The thick yellow liquid was re-dispersed in an equal volume of water and centrifuged at 14,000 rpm for 60 minutes. Again, the supernatant liquid was decanted. This washing process was repeated 6 times. The yellow liquid, containing about 4.5 g of the graphene oxide sheets, was used in the next step directly.

Preparation of a Porous Graphene Oxide Material

A porous graphene oxide material, i.e., ba-GO1, was prepared by treating the graphene oxide sheets thus made with a base and then with an acid.

The graphene oxide sheets (2.7 g) were suspended in water (1500 mL). NaOH (18 g), a base, was added into the graphene oxide suspension, which was then heated at 120° C. for 2 hours. The base-treated graphene oxide sheets, collected by centrifugation at 13,000 rpm, were mixed with water (1500 mL) and ultrasonicated for 30 minutes to obtain a homogenous solution. A HCl aqueous solution (37 wt %, 45 mL) was added into the solution, which was then heated at 120° C. for 2 hours to yield a dark-colored material. This material was filtered, washed with both water and acetone, and dried under vacuum to obtain 1.9 g of a porous graphene oxide material, i.e., ba-GO1.

Example 2

Another porous graphene oxide material, i.e., ba-GO2, was prepared following the same procedure described in Example 1 except that 25.2 g of KOH, instead of NaOH, was used.

Example 3

Still another porous graphene oxide material, i.e., ba-GO3, was prepared following the procedure described in Example 1 except that different amounts of the starting material and reagents were used.

To prepare ba-GO3, the graphene oxide sheets (0.45 g) were first suspended in water (750 mL). Base NaOH (3 g) was added to the resultant graphene oxide suspension, which was then heated at 120° C. for an hour. The base-treated graphene oxide sheets, collected by centrifuging the suspension at 13,000 rpm, were mixed with water (750 mL) and ultrasonicated for 10 minutes to make a homogenous solution. A HCl aqueous solution (37 wt %, 7.5 mL) was added into the solution, which was then heated at 120° C. for an hour to yield a dark-colored material. This material was filtered, washed with water and acetone, and dried under vacuum to obtain 0.3 g of a porous graphene oxide material, i.e., ba-GO3.

Example 4

Porous graphene oxide material ba-GO4 was prepared following the same procedure described in Example 3 except that 4.2 g of KOH, instead of NaOH, was used.

Example 5

A bifunctional catalyst containing palladium, i.e., Pd@ba-GO, was prepared following the procedure described below.

Porous graphene oxide material ba-GO3 (200 mg) prepared in Example 3 above was added to a mixture of ethylene glycol (20 mL) and DMF (10 mL). The resultant mixture was ultrasonicated for 10 hours to obtain a homogenous solution. Palladium diacetate (20 mg) was dissolved in a mixture of ethylene glycol (10 mL) and DMF (5 mL) and ultrasonicated for 1 hour. The aforementioned two mixtures were combined and stirred at room temperature. Subsequently, sodium ascorbate solution (40 mg in 10 mL of ethylene glycol and 5 mL of DMF) was added slowly to the combined mixture, which was then stirred at room temperature for 16 hours. This resultant mixture was centrifuged, washed with water (60 mL, twice) and with acetone (60 mL, 3 times), and dried in an oven at 80° C. for 16 hours to obtain 156 mg of Pd@baGO, which is loaded with 4.0 wt % of Pd.

Example 6

Another bifunctional catalyst, i.e., Au@ba-GO, which contains gold, was prepared following the same procedure described in Example 5 except that 20 mg of gold(III) chloride was used instead of Pd.

Example 7

Oxidation of primary amines was carried out using as the catalyst ba-GO3 prepared in Example 3 above.

As shown in Scheme 1, benzylamine and substituted benzylamines were oxidized to corresponding benzylidene benzylamines.

Scheme 1. Oxidation of benzylamine using ba-GO3

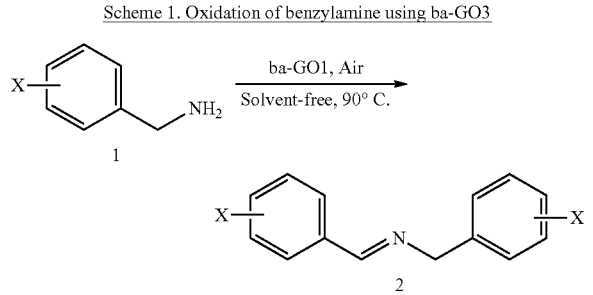

Benzylamine (1 g) and ba-GO3 (0.05 g) were stirred at 90° C. in a round-bottomed flask open to air. The reaction was monitored with a gas chromatograph. After heating for 12 hours, benzylamine was converted to benzylidene benzylamine in an unexpectedly high yield of 98%.

Catalyst ba-GO3 was recovered by filtration, rinsing with acetonitrile, and drying at 60° C. in an oven. It was reused as a catalyst for 6 cycles. Unexpectedly, at the sixth cycle, it was still capable of converting benzylamine to N-benzylidene benzylamine in a yield as high as 93%.

Substituted benzylamines (i.e., p-chlorobenzylamine, 1,2-dichlorobenzylamine, p-methylbenzylamine, m-methylbenzylamine, and o-methylbenzylamine) were oxidized following the same procedure described above. The reaction time and yield for each oxidation reaction were shown in Table 1 below.

TABLE 1

Oxidation of benzylamines using ba-GO3 as catalyst

| Entry | Substrate (Compound No) | Product (Compound No) | Reaction Time (hours) | Yield (%) |
|---|---|---|---|---|
| 1 | X = H (1a) | X = H (2a) | 12 | 98[a] |
| 2 | X = H (1a) | X = H (2a) | 12 (6th cycle) | 93[a] |
| 3 | X = p-Cl (1b) | X = p-Cl (2b) | 12 | 96[b] |
| 4 | X = 1,2-diCl (1c) | X = 1,2-diCl (2c) | 12 | 94[b] |
| 5 | X = p-Me (1d) | X = p-Me (2d) | 11 | 94[b] |
| 6 | X = m-Me (1e) | X = m-Me (2e) | 12 | 92[b] |
| 7 | X = o-Me (1f) | X = o-Me (2f) | 13 | 95[b] |

[a] Yield calculated using GC with anisole as the internal standard.
[b] Isolation yield.

In addition to benzylamines, 2-thiophenemethylamine (1 g) was oxidized using ba-GO2 (0.05 g) at 90° C. in a flask open to air. The reaction was monitored with a gas chromatograph. After heating for 12 hours, 2-thiophenemethylamine was converted to 1-(thiophen-2-yl)-N-(thiophen-2-ylmethylene)methanamine in an unexpectedly high yield of 92%, as shown below in Scheme 2.

Scheme 2. Oxidation of 2-thiophenemethylamine using ba-GO2

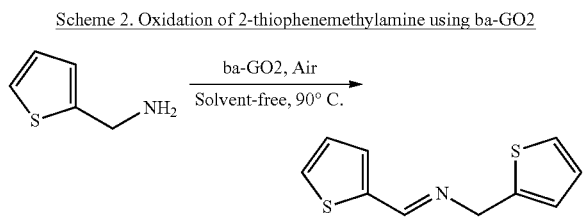

Example 8

Cross-dehydrogenative-coupling reactions were carried out using as the catalyst ba-GO3 prepared in Example 3 above.

As shown in Scheme 3 below, tertiary amine 3 (0.25 mmol), via heating with ba-GO3 (0.04 g) at 80° C., was oxidized to an imine intermediate, which was subsequently attacked by nucleophile 4 (e.g., nitromethane, 0.2 mL; and indole, 0.3 mmol) to obtain a corresponding product, i.e., one of 5a-5h. The reaction duration in hours and the yield in % for each product were shown in Scheme 3 below.

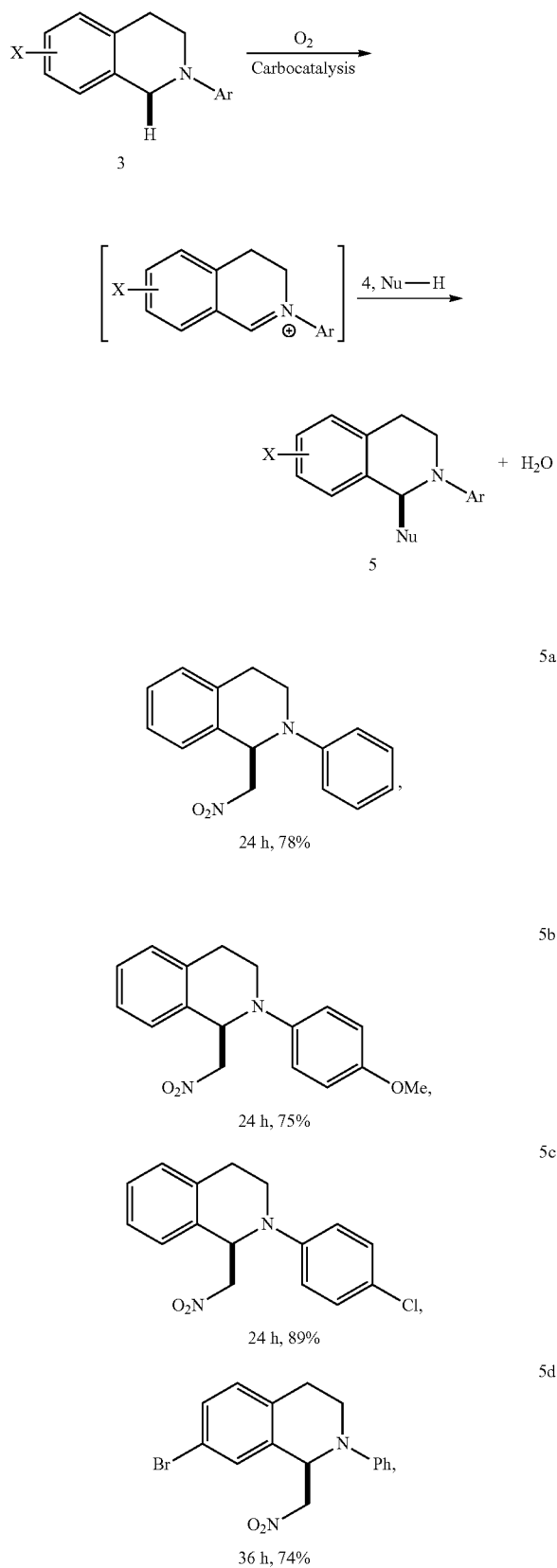
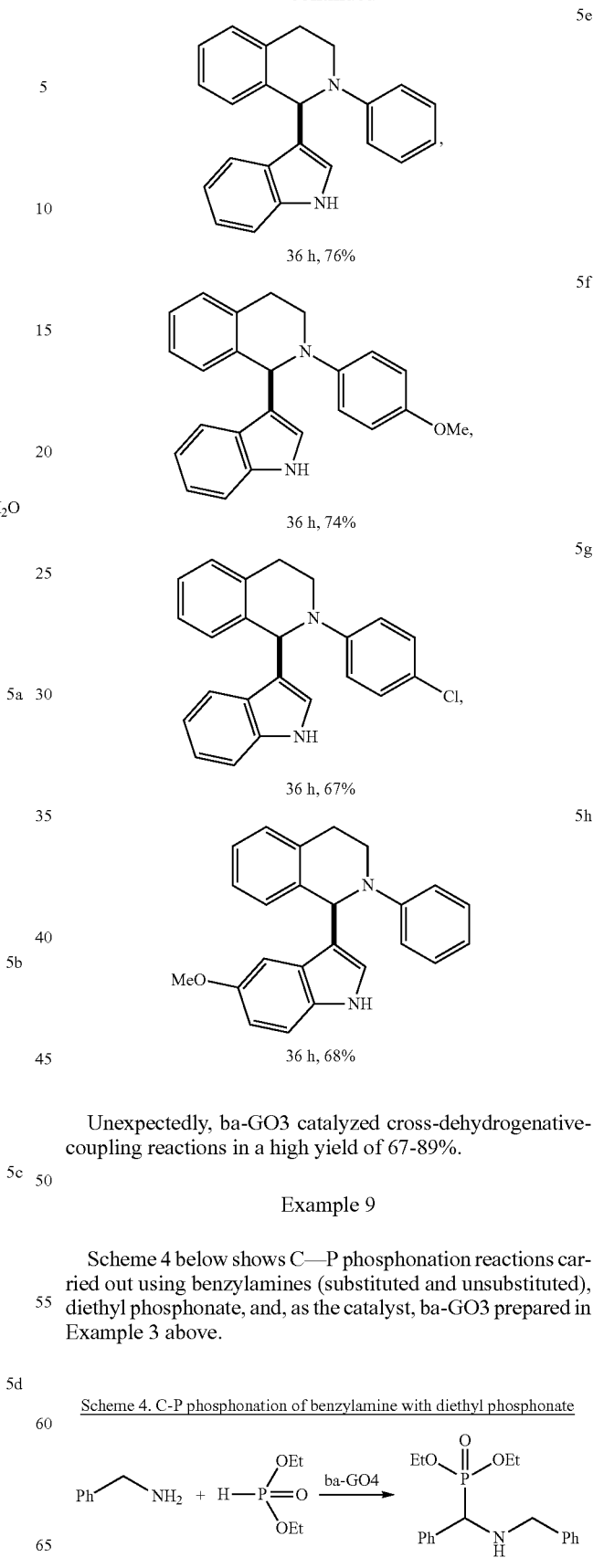
Unexpectedly, ba-GO3 catalyzed cross-dehydrogenative-coupling reactions in a high yield of 67-89%.
Example 9
Scheme 4 below shows C—P phosphonation reactions carried out using benzylamines (substituted and unsubstituted), diethyl phosphonate, and, as the catalyst, ba-GO3 prepared in Example 3 above.
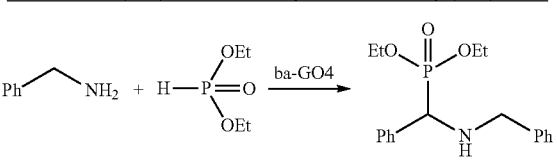

More specifically, benzylamine (1 mmol) was heated with diethyl phosphonate (1 mmol) and ba-GO3 (30 mg) at 90° C. for 8 hours to obtain diethyl(benzylamino)(phenyl)-methylphosphonate. An unexpectedly high yield of 58% was achieved.

4-Chlorobenzylamine (1 mmol) was also heated with diethyl phosphonate (1 mmol) and ba-GO3 (30 mg) at 90° C. for 8 hours to obtain diethyl(4-chlorobenzylamino) (4-chlorophenyl)methylphosphonate. Again, an unexpectedly high yield of 60% was achieved.

Each of 2-methylbenzylamine and 3-methylbenzylamine (1 mmol) was heated with diethyl phosphonate (1 mmol) and ba-GO3 (30 mg) at 90° C. for 12 hours to obtain diethyl(2-methylbenzylamino)(2-methylphenyl)methylphosphonate (with an unexpectedly high yield 58%) and diethyl(3-methylbenzylamino)(3-methylphenyl)methylphosphonate (with an unexpectedly high yield 45%).

4-Methylbenzylamine (1 mmol) was heated with ba-GO3 (30 mg) at 90° C. for 3 hours, followed by addition of diethyl phosphonate and subsequent heating at 90° C. for 8 hours to obtain (4-methyl-benzylamino)(4-methylphenyl)methylphosphonate. An unexpectedly high yield of 61% was observed.

Example 10

Oxidative condensation reactions of benzylamines (substituted and unsubstituted) were carried out using catalyst Pd@ba-GO in Example 5 above, as shown in Scheme 5 below.

Scheme 5. Oxidative condensation of benzylamine using Pd@ba-GO

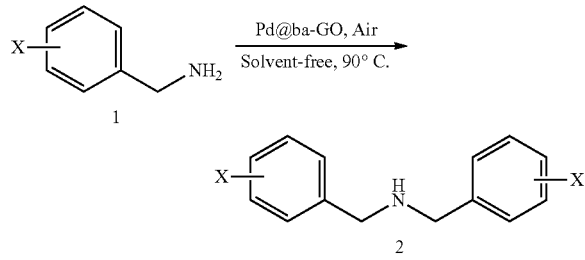

To carry out the oxidative condensation, benzylamine (0.5 mmol) was heated with catalyst Pd@ba-GO (10 mg) and solvent $CH_3CN$ (0.2 mL) at 90° C. in a flask open to air for 6 hours, and then stirred also at 90° C. under $H_2$ gas (1 atm) for 6 hours to obtain dibenzylamine. An unexpectedly high yield of 91% was achieved.

4-Methylbenzylamine (0.5 mmol) was also heated with catalyst Pd@ba-GO (10 mg) and solvent $CH_3CN$ (0.2 mL) at 90° C. in a flask open to air for 6 hours, and then stirred also at 90° C. under $H_2$ gas (1 atm) for 8 hours to obtain di-(4-methylbenzyl)amine. Again, an unexpectedly high yield of 82% was achieved.

3-Methylbenzylamine (0.5 mmol) was heated with catalyst Pd@ba-GO (10 mg) and solvent $CH_3CN$ (0.2 mL) at 90° C. in a flask open to air for 6 hours, and then stirred also at 90° C. under $H_2$ gas (1 atm) for 8 hours to obtain di-(3-methylbenzyl)amine. An unexpectedly high yield of 90% was observed.

2-Methylbenzylamine (0.5 mmol) was heated with catalyst Pd@ba-GO (10 mg) and solvent $CH_3CN$ (0.2 mL) at 90° C. in a flask open to air for 6 hours, and then stirred also at 90° C. under $H_2$ gas (1 atm) for 6 hours to obtain di-(2-methylbenzyl)amine. Again, an unexpectedly high yield of 87% was observed.

Characterization of Graphene Oxide

The graphene oxide sheets and graphene oxide material ba-GO1, both prepared in Example 1 above, were characterized using six analytical methods described below.

Scanning Electron Microscope (SEM)

The graphene oxide sheets and graphene oxide material ba-GO3 were viewed under an SEM. SEM images showed that 80% of the pores in graphene oxide sheets had a pore size of 1-2 nm and 20% of them had a pore size of 2-5 nm. By contrast, 60% of the pores in ba-GO3 had a pore size of 1-2 nm and 40% of them had a pore size of 2-5 nm.

Brunauer-Emmett-Teller (BET) Analysis

The graphene oxide sheets and ba-GO3 were subjected to BET analysis to determine the pore volume and the surface area. See Ruoff et al., Carbon, 45, 1558-65 (2007).

BET results show that the graphene oxide sheets had a surface area of 58 $m^2/g$ and a pore volume of 0.064 mL/g and that ba-GO3 had a surface area of 365 $m^2/g$ and a pore volume of 0.25 mL/g.

X-Ray Photoelectron Spectroscopy (XPS)

The graphene oxide sheets and ba-GO3 were analyzed by an X-ray Photoelectron Spectrometer. See Nguyen et al., ACS Nano, 5, 4380-91 (2011).

FIG. 1 shows the X-ray photoelectron spectra of the graphene oxide sheets (designated as GO in the figure) and ba-GO3 (designated as ba-GO in the figure). In FIG. 1(a), the peak at 285 ev corresponds to graphitic $sp^2$ carbon atoms, the peak at 287 ev corresponds to functional groups C—O—C (i.e., epoxide and ether groups) and C—OH (i.e., hydroxyl group), and the peak between 289 and 290 ev corresponds to functional group C=O (i.e., carbonyl). In FIG. 1(b), the peaks corresponding to C—OH and C—O—C decrease. This observation indicates that the base and acid treatments removed hydroxyl and epoxide groups from graphene oxide sheets, resulting in a porous graphene oxide material that is highly catalytic.

According to the XPS, the C/O ratio of ba-GO3 was 4/1.

Fourier Transform Infrared (FTIR) Spectroscopy

The graphene oxide sheets and ba-GO3 were analyzed using an FTIR spectrometer.

Figure 2:
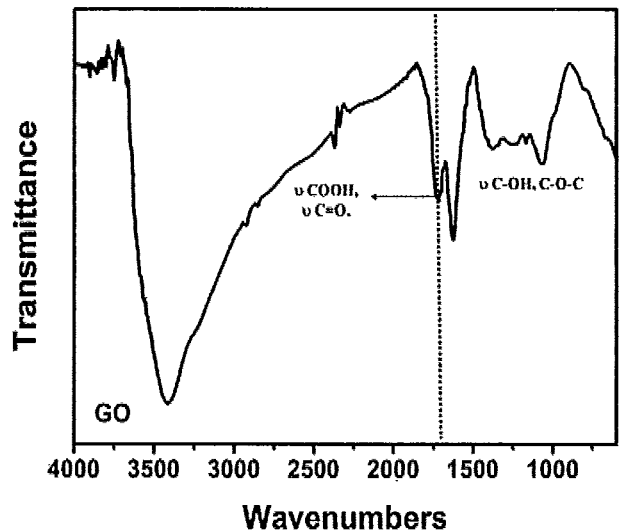
FIG. 2 shows Fourier transform infrared spectra of graphene oxide sheets and ba-GO3.
Figure 2:
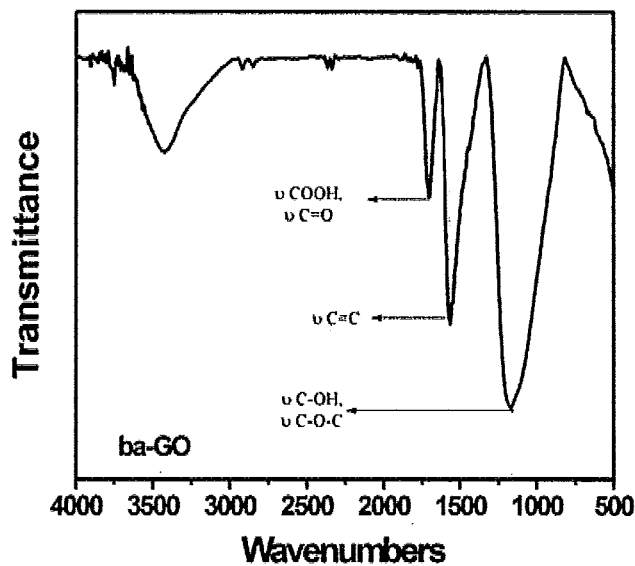

The spectra are presented in FIG. 2. FIG. 2(a) shows the spectrum of graphene oxide sheets, indicating the presence of COOH, C=O, $COO^-$, and OH, and FIG. 2(b) shows the spectrum of ba-GO3, indicating the presence of COOH, C=O, OH, and C—O—C and the absence of $COO^-$.

Thermogravimetric Analysis (TGA)

The graphene oxide sheets and ba-GO3 were subjected to TGA. The results are shown in FIG. 3, in which GO refers to graphene oxide sheets and ba-GO refers to ba-GO3.

Figure 3:
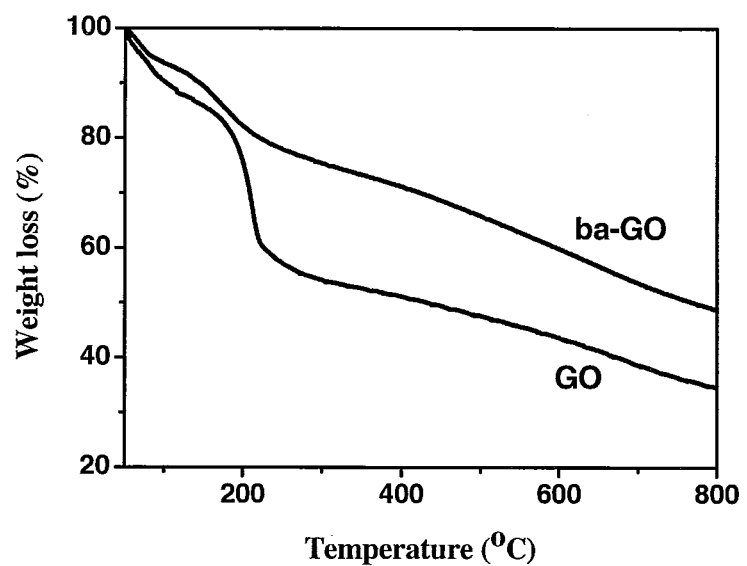
FIG. 3 shows thermogravimetric analysis results of graphene oxide sheets and ba-GO3.

As shown in FIG. 3, graphene oxide sheets had an initial mass loss at about 150° C. (the bottom curve in the figure), and further mass loss between 200 and 250° C. Unexpectedly, ba-GO3 showed a less-than-50% mass loss at 600° C. and a less-than-55% mass loss at 800° C. (the top curve in the figure). These results show that ba-GO3 was relatively thermostable.

Electron Spin Resonance (ESR)

The graphene oxide sheets and ba-GO3 were subjected to ESR analysis. The results are shown in FIG. 4, in which Figure (a) is the spectrum of the graphene oxide sheets (designated as GO in this figure) and Figure (b) is the spectrum of ba-GO3 (designated as ba-GO in this figure).

Figure 4:
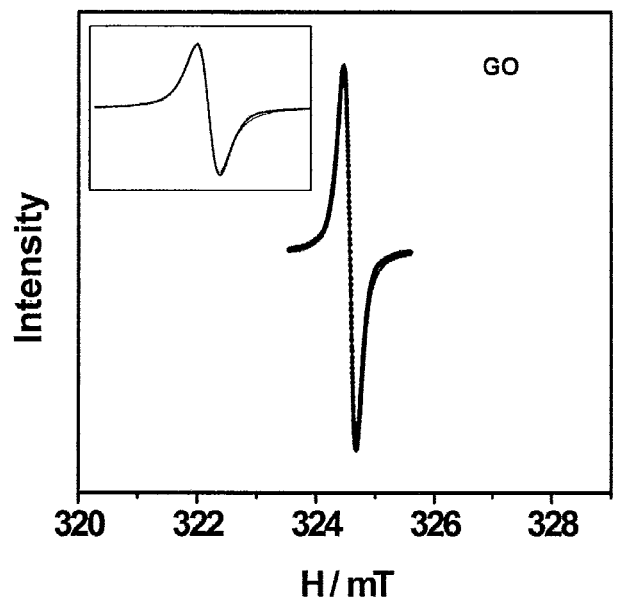
FIG. 4 shows electron spin resonance spectra of graphene oxide sheets and ba-GO3.
Figure 4:
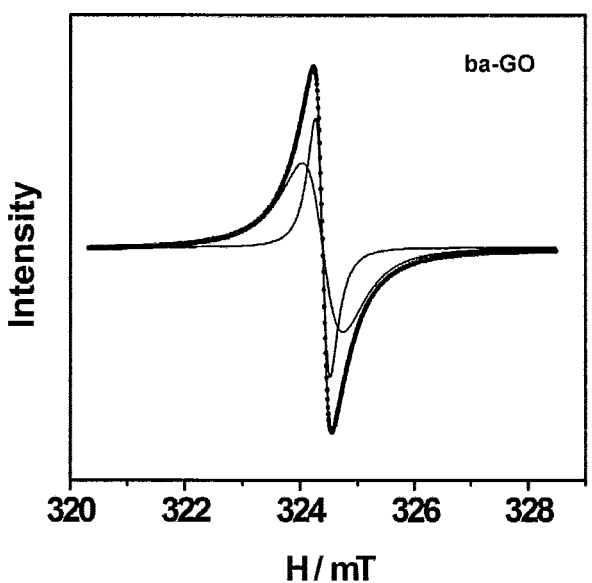

There are two types of peaks in the ESR spectra shown in FIG. 4: sharp ones having smaller linewidths and broad ones having larger linewidths. Broad peaks, which are only observed in the spectrum of ba-GO3, are the results of localized spins originating from the edge of a π-electron system in graphene oxide sheets. This observation suggests that the catalytic reactivity of ba-GO3 relates to localized spins created at the edge of a π-electron system.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of preparing a porous graphene oxide material, the method comprising:
preparing graphene oxide sheets from graphite by reacting graphite flakes with sodium nitrate, concentrated sulfuric acid, and $KMnO_4$ at 40 to 170° C.;
providing a graphene oxide suspension by suspending the graphene oxide sheets in a solvent;
heating the graphene oxide suspension with a base at 25 to 300° C. for 0.1 to 48 hours to obtain base-treated graphene oxide sheets; and
heating a mixture of the base-treated graphene oxide sheets and an acid at 25 to 300° C. for 0.1 to 48 hours to yield the porous graphene oxide material,
wherein the weight ratio of the base to the graphene oxide sheets is 1:1 to 50:1, the weight ratio of the acid to the graphene oxide sheets is 1:1 to 50:1, the base in the graphene oxide suspension has a concentration of 0.01 to 50 N, and the acid in the mixture has a concentration of 0.01 to 50 N, the base being NaOH, KOH, LiOH, $Na_2CO_3$, $CsCO_3$, $K_3PO_4$, $NaHCO_3$, n-BuLi, t-BuOK, an amine, pyridine, bi-pyridine, or a combination thereof; and the acid being HCL HBr, HI, $H_2SO_4$ or its salt, $HNO_3$, a carboxylic acid, a sulfonic acid, a phosphoric acid or its salt, $P_2O_5$, a metal chloride, or a combination thereof.

2. The method of claim 1, wherein the graphene oxide suspension is heated with the base at 60 to 170° C. for 1 to 24 hours, the base-treated graphene oxide sheets are heated with the acid at 60 to 170° C. for 1 to 24 hours, the weight ratio of the base to the graphene oxide sheets is 2:1 to 25:1, the weight ratio of the acid to the graphene oxide sheets is 2:1 to 25:1, the base in the graphene oxide suspension has a concentration of 0.02 to 20 N, and the acid in the mixture has a concentration of 0.02 to 20 N.

3. The method of claim 2, wherein the base-treated graphene oxide sheets are heated with the acid at 100 to 120° C. for 2 to 10 hours, the weight ratio of the base to the graphene oxide sheets is 3:1 to 10:1, the weight ratio of the acid to the graphene oxide sheets is 3:1 to 10:1, the base in the graphene oxide suspension has a concentration of 0.05 to 10 N, and the acid in the mixture has a concentration of 0.05 to 10 N.

4. The method of claim 2, wherein the graphene oxide suspension is heated with the base at 100 to 120° C. for 2 to 10 hours, the base-treated graphene oxide sheets are heated with the acid at 60 to 170° C. for 1 to 24 hours, the weight ratio of the base to the graphene oxide sheets is 2:1 to 25:1, the weight ratio of the acid to the graphene oxide sheets is 2:1 to 25:1, the base in the graphene oxide suspension has a concentration of 0.02 to 20 N, and the acid in the mixture has a concentration of 0.02 to 20 N.

5. The method of claim 4, wherein the base-treated graphene oxide sheets are heated with the acid at 100 to 120° C. for 2 to 10 hours, the weight ratio of the base to the graphene oxide sheets is 3:1 to 10:1, the weight ratio of the acid to the graphene oxide sheets is 3:1 to 10:1, the base in the graphene oxide suspension has a concentration of 0.05 to 10 N, and the acid in the mixture has a concentration of 0.05 to 10 N.

6. The method of claim 1, wherein the base-treated graphene oxide sheets are heated with the acid at 60 to 170° C. for 1 to 24 hours.

7. The method of claim 6, wherein the weight ratio of the acid to the graphene oxide sheets is 2:1 to 25:1, and the acid in the mixture has a concentration of 0.02 to 20 N.

8. The method of claim 6, wherein the base-treated graphene oxide sheets are heated with the acid at 100 to 120° C. for 2 to 10 hours.

9. The method of claim 8, wherein the weight ratio of the acid to the graphene oxide sheets is 3:1 to 10:1, and the acid in the mixture has a concentration of 0.05 to 10 N.

10. The method of claim 2, wherein the weight ratio of the base to the graphene oxide sheets is 2:1 to 25:1, the weight ratio of the acid to the graphene oxide sheets is 2:1 to 25:1, the base in the graphene oxide suspension has a concentration of 0.02 to 20 N, and the acid in the mixture has a concentration of 0.02 to 20 N.

11. The method of claim 10, the weight ratio of the base to the graphene oxide sheets is 3:1 to 10:1, the weight ratio of the acid to the graphene oxide sheets is 3:1 to 10:1, the base in the graphene oxide suspension has a concentration of 0.05 to 10 N, and the acid in the mixture has a concentration of 0.05 to 10 N.

12. A porous graphene oxide material having a pore size of 0.2 to 100 nm, a pore volume of 0.01 to 5 mL/g, a surface area of 20 to 2600 m$^2$/g, a C/O molar ratio of 2/1 to 10/1, and a —COO$^-$ content of 0.

13. The porous graphene oxide material of claim 12, wherein the porous graphene oxide material has a pore size of 0.5 to 50 nm, a pore volume of 0.05 to 1 mL/g, a surface area of 50 to 1000 m$^2$/g, and a C/O molar ratio of 5/2 to 8/1.

14. The porous graphene oxide material of claim 13, wherein the porous graphene oxide material has a pore size of 1 to 20 nm, a pore volume of 0.1 to 0.4 mL/g, a surface area of 100 to 600 m$^2$/g, and a C/O molar ratio of 3/1 to 6/1.

15. The porous graphene oxide material of claim 12, further comprising a catalyst selected from the group consisting of Pd, Pt, Au, Cu, $V_2O_5$, Co, Rh, Ru, Ni, and Fe.

16. A porous graphene oxide material prepared by the method of claim 1, wherein the porous graphene oxide material has a pore size of 0.2 to 100 nm, a pore volume of 0.01 to 5 mL/g, a surface area of 20 to 2600 m$^2$/g, a C/O molar ratio of 2/1 to 10/1, and a —COO$^-$ content of 0.

17. The porous graphene oxide material of claim 16, wherein the porous graphene oxide material is prepared by the method of claim 5.

18. The porous graphene oxide material of claim 16, wherein the porous graphene oxide material is prepared by the method of claim 9.

19. A process of carrying out a chemical reaction by agitating a reaction medium containing a reactant or reactants, and a catalyst that is the porous graphene oxide material of claim 12, wherein the chemical reaction is an oxidation reaction, a reduction reaction, a Suzuki coupling reaction, an oxygen reduction reaction, or an oxidation-reduction tandem reaction, the reactant or reactants being alcohols, amines, alkenes, or alkanes.

20. The process of claim 19, wherein the chemical reaction is an oxidation reaction, the porous graphene oxide material is 1 to 200 wt % of the reactant or reactants, and 20 to 98% of the reactant or reactants are converted to a product.

21. A process of carrying out a chemical reaction by agitating a reaction medium containing a reactant or reactants, and a catalyst that is the porous graphene oxide material of claim 16, wherein the chemical reaction is an oxidation reaction, a reduction reaction, a Suzuki coupling reaction, an oxygen reduction reaction, or an oxidation-reduction tandem reaction, the reactant or reactants being alcohols, amines, alkenes, or alkanes.

22. The process of claim 21, wherein the chemical reaction is an oxidation reaction, the porous graphene oxide material, 2 to 20 wt % of the reactant or reactants, is the material of claim 17, and 20 to 98% of the reactant or reactants are converted to a product.

\* \* \* \* \*